US008877465B2

(12) United States Patent
Geiringer et al.

(10) Patent No.: US 8,877,465 B2
(45) Date of Patent: Nov. 4, 2014

(54) PRODUCTION OF ULTRAPURE EPA AND POLAR LIPIDS FROM LARGELY HETEROTROPHIC CULTURE

(75) Inventors: Karl Thomas Geiringer, Auckland (NZ); Hywel David Griffiths, Auckland (NZ)

(73) Assignee: Photonz Corporation Limited, Auckland (NZ)

( * ) Notice: Subject to any disclaimer, the term of this patent is extended or adjusted under 35 U.S.C. 154(b) by 1491 days.

(21) Appl. No.: 12/307,532

(22) PCT Filed: Jul. 5, 2007

(86) PCT No.: PCT/NZ2007/000172
§ 371 (c)(1),
(2), (4) Date: Nov. 5, 2009

(87) PCT Pub. No.: WO2008/004900
PCT Pub. Date: Jan. 10, 2008

(65) Prior Publication Data
US 2010/0069492 A1 Mar. 18, 2010

(30) Foreign Application Priority Data
Jul. 5, 2006 (NZ) .......................................... 548339

(51) Int. Cl.
*C12P 7/64* (2006.01)
(52) U.S. Cl.
CPC ............. *C12P 7/6472* (2013.01); *C12P 7/6427* (2013.01)
USPC ............................................ 435/134; 435/41

(58) Field of Classification Search
None
See application file for complete search history.

(56) References Cited

U.S. PATENT DOCUMENTS

| 5,077,202 | A | * | 12/1991 | Seto et al. ................... | 435/134 |
| 5,767,095 | A | * | 6/1998 | Winget ........................ | 514/25 |
| 6,140,365 | A | | 10/2000 | Kiy et al. | |
| 2002/0001833 | A1 | * | 1/2002 | Ruecker et al. ............. | 435/134 |
| 2005/0129739 | A1 | * | 6/2005 | Kohn et al. .................. | 424/442 |

FOREIGN PATENT DOCUMENTS

| AU | 2004235641 | | 1/2005 |
| DE | 19629433 | | 1/1998 |
| JP | 59-046225 | | 3/1984 |
| JP | 2097393 | | 4/1990 |
| JP | 2001139981 | A * | 5/2001 |
| WO | WO 91/14427 | A | 10/1991 |
| WO | WO 95/24459 | | 3/1994 |
| WO | WO 2004/064716 | | 1/2004 |
| WO | WO 2004/033698 | A2 | 4/2004 |
| WO | WO 2006031699 | A2 * | 3/2006 |
| WO | WO 2006/085144 | A2 | 8/2006 |

OTHER PUBLICATIONS

Derwent abstract of JP2001-139981A, published May 22, 2001. 3 pages.*
UTEX The Culture Collection of Algae, Media Detail: LDM Medium. [online]. [retrieved on Oct. 23, 2003]. Retrieved from the Internet< URL: http://web.biosci.utexas.edu/utex/mediaDetail.aspx?mediaID=52>. 1 page.*
Wen, Z et al. Perfusion culture of the diatom *Nitzschia laevis* for ultra-high yield of eicosapentaenoic acid. Process Biochemistry. 2002. 38: 523-529.*
Wen, Z et al. Production potential of eicosapentaenoic acid by the diatom *Nitzschia laevis*. Biotechnology Letters. 2000. 22: 727-733.*
Lebeau, T et al. Diatom cultivation and biotechnologically relevant products. Part I: Cultivation at various scales. Appl. Microbiol. Biotechnol. 2003. 60: 612-623.*
Cohen, Z et al. Preparation of eicosapentaenoic acid (EPA) concentrate from Porphyridium cruentum. JAOCS. 1991. 68(1): 16-19.*
Reis, A et al. Eicosapentaenoic acid-rich biomass production by the microalga *Phaeodactylum tricornutum* in a continuous-flow reactor. Biotechnology Technology. 1996. 55: 83-88.*
Terasaki, M et al. Glycerolipid acyl hydrolase activity in the brown alga *Cladosiphon okamuranus* Tokida. Biosci. Biotechnol. Biochem. 2003. 67(9): 1986-1989.*
Bligh, Eg et al. A rapid method of total lipid extraction and purification. Canadian Journal of Biochemistry and Physiology. 1959. 37(8): 911-917.*
Cohen, Z et al. "Searching for PUFA-rich Microalgae." in: Cohen, Z et al., Single Cell Oil. [online]. Champaign, Illinois: AOCS Press, 2005. [retrieved on Nov. 4, 2012] Retrieved from the Internet: <URL: http://www.crcnetbase.com/doi/abs/10.1201/9781439822364.ch4>. 22 pages.*
Chu, W et al. Environmental effects on growth and biochemical composition of *Nitzschia inconspicua* Grunow. Journal of Applied Phycology. 1996. 8: 389-396.*

(Continued)

*Primary Examiner* — Allison Ford
*Assistant Examiner* — Susan E Fernandez
(74) *Attorney, Agent, or Firm* — Pearl Cohen Zedek Latzer Baratz LLP (57) ABSTRACT

Eicosapentaenoic acid (EPA) compositions and EPA-rich polar lipids for prophylactic or therapeutic applications are described. Production from certain cultured micro-organisms (like *Nitzschia laevis*) promotes synthesis of EPA, including polar lipids including EPA. The EPA-rich polar lipids themselves may be used as polar compounds. EPA can be selectively hydrolysed from particular positions in isolated polar lipids by lipase activity, then optionally further purified. The process bypasses reliance on diminishing fish stocks and on physico-chemical processes that may not adequately separate desirable n-3 HUFAs from unwanted products like DHA also found in fish oil and cultured organisms.

13 Claims, No Drawings

(56) References Cited

OTHER PUBLICATIONS

Figure 1:
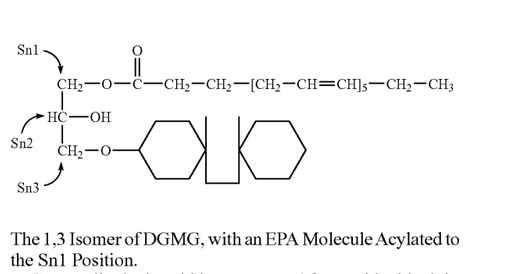

Chu, W et al. Studies on the production of useful chemicals, especially fatty acids in the marine diatom *Nitzschia conspicua* Grunow. Hydrobiologia. 1994. 285: 33-40.*

"Screening of diatoms for heterotrophic eicosapentaenoic acid production", (Tan, Chor Koon; John's Michael R.) Journal of Applied Phycology, (1996) vol. 8, No. 1, pp. 59-64, ISSN:0921-8971.

"Heterotrophic production of eicosapentaenoic acid by microalgae", Wen Zhi-You and Feng Chen; (Biotechnology Advances, (Jul. 2003) vol. 21, No. 4, pp. 273-94. Ref:97 Journal Code; 8403708. ISSN:0734-9750.

"Modelling of eicospentaenoic acid. (EPA) production from *Phaeodactylum tricornumtum* cultures in tubular photobioreactors. Effects of dillution rate, tube diameter, and solar irradiance", Fernandez F G; Perez J A; Sevilla J M; Camacho F G; Grima E M; ( Biotechnology and bioengineering, (Apr. 20, 2000) vol. 68, No. 2 pp. 173-83, Journal Code: 7502021, ISSN:0006-3592).

"Heterotrophic production potential of omega-3 polyunsaturated fatty acids by microalgae and algae-like microorganisms", Vazhappily, R and Chen, F. (Botanica Marina, (Nov. 1998) vol. 41, No. 6, pp. 553-558, ISSN:0006-8055).

"Bioreactor Technology for Production of Valuable Algal Products", Cheng Feng (Chinese Journal of OCeanology and Limnology, (1998) vol. 16, No. Suppl.,pp. 84-90, ISSN: 0254-4059).

"Application prospect and research advances in heterotrophic production of eicosapentaenoic acide by microalgae", Liu., Hong-Tai; Hu, Zhi-Jun; Hou, Giu-Qin; Wang, Jian Ren; Xue, Le-Xun (Zhongguo Yaowu (2004), 2(4), 252-256, ISSN: 1672-3651.

Derwent Abstract Accession No. 98-101721/10, B05 CO3 D16 & DE 19 629 433 A1 (Hoechst AG) Jan. 29, 1998.

Derwent Abstract Accession No. 90-152269/20 B05 C01 D16 E11 (D13 D21) & J 02097393 A(Sagami Chem Res Centre (TOYJ)) Apr. 9, 1990.

Derwent Abstract Accession No. 90-214251/28, D16 E17 & J02-145191 A(Sagami Chem Res Centre (TOYJ)) Jun. 4, 1990.

Derwent Abstract Accession No. 84-103987/17, B04 D16 & J59-046225 A(Ind Res Inst of Japan (NISH-)) Mar. 15, 1984.

Wen Z-Y et al, "Heterotrophic production of eicosapentaenoid acid by the diatom *Nitzschia laevis*: Effects of silicate and glucose" Journal of Industrial Microbiology and Biotechnology, vol. 25, No. 4, Oct. 2000, pp. 218-224.

Wen Zhi-You et al, "Application of statistically-based experimental designs for the ptimisation of eicosapentaenoic acid production by the diatom *Nitzshia Laevis*", iotechnology and Bioengineering, vol. 75, No. 2, Oct. 20, 2001, pp. 159-169.

Supplementary European Search Report for European Application EP 07 80 8670 Issued Jan. 13, 2012.

Wen Z-Y et al., "High cell density culture of the diatom *Nitzschia laevis* for eicosapentaenoic acid production: fed-batch development", Process Biochemistry 37 (2002) 1447-1453.

* cited by examiner

PRODUCTION OF ULTRAPURE EPA AND POLAR LIPIDS FROM LARGELY HETEROTROPHIC CULTURE

CROSS-REFERENCE TO RELATED APPLICATIONS

This is a national stage application of PCT/NZ2007/000172, filed on Jul. 5, 2007, which claims priority to New Zealand patent application 548339, filed on Jul. 5, 2006, which are incorporated herein by reference.

FIELD

This invention relates to lipid compositions synthesized by single-cell organisms, to the manufacture and some applications of omega-3 highly unsaturated fatty acids and to pharmaceutical substances, and in particular to novel therapeutic, dietary and health-food compositions.

DEFINITIONS

Alpha linolenic acid is an omega-3 fatty acid with eighteen carbon atoms and three double bonds.

Arachidonic acid is an omega-6 fatty acid with twenty carbon atoms and four double bonds.

Diacyl galactolipids are galactolipids with both Sn1 and Sn2 occupied by fatty acid molecules.

Digalactosyl galactolipids are those where two galactose molecules are attached.

Docosopentaenoic acid is an omega-3 fatty acid with twenty-two carbon atoms and five double bonds.

Docosahexanoic acid is an omega-3 fatty acid with twenty-two carbon atoms and six double bonds.

Eicosapentaenoic acid is an omega-3 fatty acid with twenty carbon atoms and five double bonds.

Effective amount means: an amount sufficient to cause a desired result when administered.

EPA-only means: a composition containing in its highly unsaturated omega-3 fatty acid component, substantially only EPA.

Esterification of n-3 HUFAs is understood, so that a term such as "99% pure EPA" is understood to take no account of the ethyl or other moiety used to form an ester with the free fatty acid.

Nutraceutical is any substance that is a food or a part of a food and provides medical or health benefits, including the prevention and treatment of disease.

Purity: 1. Chemical purity: The EPA composition is substantially free of all molecules other than EPA.

2. Functional purity: The EPA composition is substantially free of those materials herein defined as "undesired". An EPA composition according to this definition of purity may include only 1 to 10% EPA (although more preferably 60-90% EPA; the remainder may include galactolipids or components thereof, or added pharmaceutically acceptable excipients, anti-oxidants, adsorbents, flavours, and the like.

3. Pharmaceutical purity: refers to EPA-rich compositions comprising around 90% of EPA or more by weight and simultaneously a ratio of EPA to any individual undesired molecule of at least around 90 to 1.

Undesired molecules or materials are defined as those that may diminish the desired beneficial health effect of EPA-rich compositions when co-consumed. These include molecules that may diminish the desired effect through actions which may be antagonistic, competitive, block, reverse, mediate, synergise or otherwise alter the desired beneficial health effect of EPA when consumed in an effective (or clinically relevant) amount. For the purposes of the present specification undesired molecules are to include structurally or functionally similar molecules including fatty acids, docosohexaerioic acid (DHA), arachidonic acid (AA), 18:4 n-3, 18:3 n-3, 18:2 n-6 and other omega-3 and 6 fatty acids in general. AA is a precursor of EPA.

EPA-rich means that the composition includes more than 1% of EPA as dry weight.

EPA productivity means the amount of EPA which can be produced per unit cost. A proxy measure for productivity in largely heterotrophic cultures of microalgae culture is often taken as the combined effect of yield, growth rate, cell density, nutrient utilisation efficiency, and dilution rate.

Fatty acid compositions include—ethyl esters, salts, free fatty acids, methyl esters, and other alcohol esters of fatty acids, and combinatorial lipids.

Galactolipids are comprised of a glycerol backbone with at least two separate molecules attached; at least one of which is a fatty acid and the other is, either one or two molecules of galactose (in mono or disaccharide form) bonded by, in the case of the fatty acid or fatty acids, an ester link or rarely an ether link and in the case of the galactose or galactoses an ether link in all cases. At least one galactose is present and normally attached to the Sn3 position of glycerol. The galactose is always in pyranose form. A second and rarely a third galactose molecule is attached by beta-d-3-pyranosyl bonds to the preceding galactose molecule. Positions are labeled according to a convention based on an original stereospecific structure (see table 1 showing the 1.3 isomer of the DGMG galactolipid class containing an EPA molecule acylated in the Sn1. Normally when only one fatty acid molecule is attached it occupies the Sn1 position. However, occasionally one fatty acid may be attached in the Sn2 position while the Sn1 position remains unoccupied. This may be referred to as a lyso derivative.

The 1,3 Isomer of DGMG, with an EPA Molecule Acylated to the Sn1 Position.

Gamma linolenic acid is an omega-6 fatty acid with eighteen carbon atoms and four double bonds.

Heterotrophic culture means a culture of organisms for which the sole energy source is derived from supplied nutrients (the major nutrient group for energy metabolism) which is usually a form or forms of organic carbon (e.g. glucose, acetate).

Largely (or partially) heterotrophic culture means a mixotrophic culture of organisms for which the major energy source is derived from supplied nutrients (the major nutrient group for energy metabolism) which is usually a form or forms of organic carbon (e.g. glucose, acetate) and the minor energy source for energy metabolism is light.

Linoleic acid is an omega-6 fatty acid with eighteen carbon atoms and two double bonds.

Monoacyl galactolipids are galactolipids with only one position occupied by a fatty acid. In a monoacyl galactolipid the fatty acid molecule is attached either at position Sn1 or Sn2.

Monogalactosyl galactolipids are those with only one galactose molecule attached.

Neutral lipids are those lipids contained in an organism which can be isolated through the use of non-polar solvents and include mono-di- and triacylglycerols Photosynthetic lipids are those polar lipids whose production can be significantly altered via the addition of light to a largely heterotrophic culture of microorganisms. These may occur within the chloroplast as is predominantly the case with galactolipids or may also be associated with other cell organelles as is predominantly the case with phospholipids.

Polar lipids are those lipids contained in an organism which can be isolated through the use of polar solvents and include phospholipids and galactolipids Photosynthetically active average irradiance inside a culture is the amount of electromagnetic radiation between wavelengths 400 nm and 700 nm incident on a culture averaged over all positions in the culture vessel and over time.

Stearidonic acid is an omega-3 fatty acid with eighteen carbon atoms and four double bonds.

Sub-photosynthetic exposure means an exposure to light whereby the combination of intensity and exposure time is equal or less than around the equivalent of a continuous illumination of 1 to about 10 micromol photons per square meter per second.

Omega-3 fatty acid is a fatty acid with the first double bond three carbon atoms from the n-methyl end of the molecule.

Omega-6 fatty acid is a fatty acid with the first double bond six carbon atoms from the n-methyl end of the molecule.

ABBREVIATIONS

18:2 n-6 or LA: linoleic acid
18:3 n-3 or ALA: alpha linolenic acid
18:4 n-3 or SDA: stearidonic acid
18:4 n-6 or GLA: gamma linolenic acid
20:4 n-6 or AA: arachidonic acid
20:5 n-3 or EPA: eicosapentaenoic acid
22:5 n-3 or DPA: docosopentaenoic acid
22:6 n-3 or DHA: docosohexaenoic acid
DGDG digalactosyldiacylgalactolipid
DGMG: digalactosylmonoacylgalactolipid
LPC: Lysophosphatidylcholine
n-3: omega-3
n-6: omega-6
n-3 HUFA: omega-3 highly unsaturated fatty acid
MGMG: monogalatosylmonoacylgalactolipid
MGDG monogalactosyldiacylgalactolipid
*N. laevis*: *Nitzschia laevis* (UTEX 2047)
*N. alba*: *Nitzschia alba*
PC: Phosphatidylcholine
LPC: Lysophosphatidylcholine
PG: Phosphatidylglycerol
PE: Phosphatidylethanolamine
SQDG: sulfoquinovosyl diacylglycerol

BACKGROUND

It was discovered in the late 1920s that certain "essential" dietary fatty acids must be present in effective quantities for normal growth and health in rats to ensue (Burr & Burr J. Biol. Chem., 82: 345-367 1929). Epidemiological data collected from human populations beginning in the 1940s then suggested relatively high dietary intakes of n-3 HUFA may be protective against the development of a number of medical conditions and that low n-3 intake may increase risk (Sinclair. Lancet 1:381-3 1956; Bang et al., Lancet 1:1143-5.1971; Hirai of al., Lancet 2:1132-3. 1980; Kromhout of al Am J. Clin. Nutr., 85:1142-1147).

In recent decades supplementation studies incorporating individual omega-3 highly unsaturated fatty acids (n-3 HUFA) in the diet of humans have demonstrated beneficial health effects of individual dietary n-3 HUFA. In particular, human dietary supplementation studies incorporating relatively pure forms of the n-3 HUFA eicosapentaenoic acid (EPA) have suggested this nutrient may promote health and ameliorate or even reverse the effects of a range of common diseases, including but not limited to certain forms of cardiovascular disease and depression (Yokoyama et al., Lancet 369:1062-1063. 2007; Peet & Horrobin Arch. Gen. Psych. 59(10) 913-9 2002).

The therapeutic effect of dietary supplementation with concentrated forms of EPA are dependent to some extent on purity. High purity dose forms have an advantage in terms of increased bioavailability. Furthermore the desired effects of EPA are limited or even reversed by the co-consumption of undesired molecules; (as herein defined) in particular docosohexaenoic acid (DHA); also AA and other omega-3 and 6 fatty acids in general. Therefore to enable effective pharmaceutical or therapeutic use of EPA, high purity dose forms, free of the undesired molecules, are required.

Should the demand for high purity EPA increase, which seems likely, large numbers of clinically or subclinically diseased persons may come to depend on continuity of supply long term to maintain quality of life. To date, however, commercial manufacturers have not been capable of economically producing EPA-only compositions with relatively high EPA purities which are at the same time devoid of undesired molecules.

Reasons include: (1) The raw material for commercial production is exclusively limited to particular fish oils containing high levels of undesired molecules. (2) The undesired molecules contained in fish oil are structurally or physicochemically similar to EPA and cannot be easily removed during purification (3) The cost of further purification rises in a non-linear fashion with increasing purity.

Consequently even at EPA purities up to around the high 90th percentile up to 1% or more of these undesired molecules may remain.

Purification processes are also rendered less efficient by the relatively complex mixture of fatty acids, and a high degree of natural variability contained in fish oil.

The practical effect of the abovementioned factors is that commercial products currently available that contain high purity EPA may also contain unacceptably high concentrations of the abovementioned undesired molecules for therapeutic use. Furthermore the high cost of purifying fish oil to an extent where only small amounts of undesired molecules remain constrain the use of these ultrapure compositions.

Up to 15 kgs of high EPA fish oil are required to produce 1 kg of highly purified EPA in current purification processes. Because the efficiency of such manufacturers is sensitive to the initial concentration of EPA these are based on fish caught with a high percentage of EPA in their lipids. The fish oil must also be carefully handled and stored during processing to protect against damage which can result in the formation of unacceptable molecular species such as trans EPA which is an unacceptable contaminant in therapeutic formulations and virtually impossible to remove during purification. The complex structure of the fishing industry, the careful handling requirements and the dwindling and finite resource of high EPA fish species means that production of high purity EPA from sea fish is difficult to scale up in order to meet increasing demands and is likely to be unsustainable.

Many publications have reported the potential of alternative sources of EPA-rich compositions or EPA produced from cultured microbes including (micro)algae, fungi, and bacteria. Some of these sources contain low levels of undesired fatty acids. Additionally, the generally less complex fatty acid composition of microbes as compared to fish oil may offer advantages in purification. Variation in fatty acid composition in cultured microorganisms is minimal as compared to fish oil conferring an additional advantage for purification. Production of EPA-rich compositions in biotechnological processes is likely to be rapidly scalable and provide EPA-rich compositions suitable for both nutritional and therapeutic use that are of consistent quality.

The majority of the publications relating to production of EPA from microalgae concern the development of outdoor production systems. The advantage of these systems is the main source of energy for growth,—sunlight, is free. Outdoor production systems however suffer from several key deficiencies. Firstly contamination from competing microorganisms limits the applicability of open pond or raceway cultures to species which are able to withstand environmental conditions that limit the growth of other competing microorganisms. Secondly "photobioreactor" production systems designed to restrict contamination require very large surface to volume ratios to facilitate penetration of light into the culture creating a requirement for large upfront capital expenditure in the establishment of these systems and an ongoing technical challenge and cost with regard to maintaining sterility.

A further weakness of largely photosynthetic cultures developed to date is that species have not yet been isolated that accumulate significant quantities of intracellular lipid in the form of triglycerides when produced photosynthetically. This limits EPA production to that accumulated in polar lipids, the upper limit of which appears to be under tight physiological regulation.

Mixotrophic production systems have been proposed for production of EPA-rich microorganisms. These provide a proportion of the energy for growth in the form of organic carbon supplied to the culture medium. An advantage of mixotrophy includes higher productivities than are achievable with solely photosynthetic production and potentially also lower the overall requirement for light. A disadvantage of the addition of organic carbon sources to outdoor photobioreactor cultures however is the creation of an additional contamination risk by presenting a substrate for growth of non-photosynthetic contaminating organisms.

A number of solely heterotrophic systems for producing EPA-rich microorganisms have been disclosed. These overcome many of the limitations of photosynthetic systems due to their ability to achieve growth of EPA rich species in the absence of light. By eliminating the requirement for light it is possible to significantly reduced the surface-to-volume ratio of reactors and consequently also reduce capital expenditure and sterilisation costs. An additional advantage of heterotrophic production systems is that culture parameters can be tightly controlled leading to production of a product of a consistent quality.

Lipid Classes and Fatty Acid Profile

The fatty acid composition of certain EPA-rich microalgae contain low proportions of fatty acids with structural similarity to EPA. Together with the generally less complex fatty acid composition of microalgae this may offer advantages in terms of purification over fish oil.

In addition to achieving a favorable overall fatty acid composition in cultured EPA-rich microalgae the selective production of EPA in particular lipid classes is also possible.

One particular strategy for enhancement of lipid and overall EPA production in EPA-rich microalgal species is the timed imposition of a nitrogen limitation in microbial culture medium in heterotrophic cultures of microalgae. When microorganisms are deprived of key nutrients required for synthesis of membranes, lipids may be accumulated in the form of triglyceride, a lipid class not utilized extensively in lipid membrane structure.

EPA-rich triglycerides are of potential therapeutic value. EPA may be recovered from triglycerides and further purified via an array of conventional and emerging techniques. Processes designed to extract, concentrate or purify EPA-rich lipid or fatty acid compositions from triglycerides however may be disadvantaged by the presence of a relatively high level and wide range of undesirable fatty acid molecules, and a low level of stereospecificity in terms of the location of EPA within the triglycerides.

Certain polar lipid classes produced in cultures of microalgae are relatively rich in EPA. At the same time some of these lipid classes may exhibit a high degree of stereospecificity in terms of the location of EPA within the class and its isomers. This concentration of EPA in a predictable manner in particular lipid classes provides an additional opportunity to sequester undesirable molecules in unused fractions during a purification process. In addition certain lipid classes produced by cultures of microalgae may also have therapeutic value in their own right.

It may seem surprising then that little, if any, attention has been given to the possibility of inducing heterotrophic or largely heterotrophic cultures of microalgae to localise EPA in polar lipid reservoirs in such a way as to enhance the efficiency and applicability of extraction, concentration and purification processes and to provide a source of polar lipid for incorporation into therapeutic products. In fact prior art disclosures appear to teach away from this possibility.

Unfortunately until now strategies applied to enhancing the productivity of processes providing alternative sources of EPA-rich compositions have led to a reduction in the polar lipid content of EPA-rich microorganisms.

Microalgae produce two major types of polar lipids;— phospholipids and glycolipids. All these major polar lipid classes comprise a glycerol backbone with three positions conventionally labeled Sn 1-3. Phospho and galacto lipid classes are categorised respectively according to phosphate- and galactose-containing functional groups which are attached to the glycerol backbone usually at the Sn-3 position. Fatty acids are acylated at one or more positions 1-2. Isometric forms of these lipid classes arise from acylation patterns where not all available positions are occupied by fatty acids or where a functional group is attached at an alternative position.

Galactolipids are produced predominantly in the chloroplast and are a structural component of the photosynthetic membrane. Galactolipids are one of the most polar of all the lipid classes; there is a substantial difference in charge distribution over the molecule because of the polar nature of the one or more galactose moieties that are attached to the glycerol backbone, providing spatially separated centres of positive and negative charge. Hence galactolipids have found application as emulsifying agents and have been proposed as drug delivery conjugates.

The polar nature (among other physiochemical properties) of galactolipids leads to a number of useful opportunities, including but without limitation to potential advantageous routes for extraction and purification of galactolipids and galactolipid fatty acids, formulation of galactolipids and galactolipid fatty acids into foods, functional foods, beverages, pharmaceutical and industrial compositions, delivery of galactolipids and galactolipid fatty acid nutritional and therapeutic products in a bioavailable form, as well as advantageous therapeutic effects and mechanisms of action their use may promote.

Phospholipids are major structural components of cellular membranes. The highly polar 'head' of the molecules coupled with their hydrophobic fatty acid 'tails' lead the phospholipids to spontaneously form micelles and bilayers in aqueous media. Phospholipids both within and external to the chloroplast are expected to play a number of important roles in relation to the physiological response of microorganisms to light. For example it has been proposed that fatty acids located in cytoplasmic phospholipids classes are a reservoir for incorporation into chloroplastic lipids during production of photosynthetic membranes. The polar nature of phospholipids among other physiochemical properties presents a number of useful opportunities similar to those stated above for galactolipids. Certain phospholipids including PC are known to be absorbed differentially in mammals which could be turned to a therapeutic advantage. Work on absorption of galactolipids in particular MGDG in mammals is limited.

Prior Art

Culture:

Cohen et al. *Journal of Applied Phycology* 5: 109-115, 1993 disclose a general scheme for obtaining microalgal galactolipids and producing compositions enriched with the fatty acid GLA. The method disclosed involves extracting the total lipids of the organism and then separating the galactolipids from the total lipid fraction. These authors recognise in the same prior art publication that in order to be industrially useful the content of GLA in the microalgae (and presumably in the galactolipid fraction) would have to be increased. The organisms used in this study were grown under totally photosynthetic conditions. To our knowledge, prior to the present invention neither Cohen and colleagues nor any other previous authors have suggested that the required increases in yield could be accomplished by using largely heterotrophic growth.

Kyle at al in U.S. Pat. No. 5,567,732 disclose a method for producing EPA-rich oils from cells of the diatom *Nitzschia alba* in the dark and teach that it is possible to induce this organism in heterotrophic culture to enter an oleogenic phase by allowing nitrogen depletion to occur and after 12-24 hours allowing a silicate depletion state to also occur, while continuing to supply other nutrients to the culture. The colourless species of diatoms are preferred. (Colourless species in general and in particular the microorganism preferred by Kyle at al are colourless because they do not exhibit the phenotype of photosynthetic pigments. *N. alba* for example is believed to be an obligate heterotroph which means that it does not have any active photosynthetic capacity. Nevertheless, a published lipid class analysis of *N. alba* reports that a few percent of the lipid composition are comprised of galactolipids.) The authors claim that diatoms can successfully be economically cultivated to produce large quantities of single cell oil and they state "for the purposes of this specification, single cell oil means a triglyceride product of a unicellular microorganism". To our knowledge prior to the present invention neither Kyle et al nor previous authors to our knowledge have disclosed heterotrophic or largely processes useful in the commercial co-production of EPA-rich polar lipids.

The mixotrophic production of the EPA-rich microalga *Phaeodactylum tricornutum* in a tubular photobioreactor is disclosed in Ceron Garcia et al *Journal of Applied Phycology* 12: 239-248, 2000. This manufacture utilizes 9.2 g L$^{-1}$ glycerol as an organic carbon source and supplies an external irradiance of 165 µmol photons m$^{-2}$ s$^{-1}$ to the photobioreactor surface. These authors claim that by reducing the need for light this form of mixotrophic growth has a number of advantages including the possibility of greatly increasing the algal cell concentration and EPA productivity in outdoor mass culture on a large-scale. Ceron Garcia and colleagues did not however identify the advantages of largely heterotrophic growth in terms of increased polar lipid production. Furthermore neither these authors nor any previous authors have identified 290 the potential for utilizing relatively low levels of irradiance in largely heterotrophic culture for producing EPA-rich microorganisms.

A number of prior art publications have disclosed that culture conditions including light intensity and wavelength can enhance lipid and overall EPA production in specified EPA-rich microalgal species. However, prior to the present invention it had not been proposed that sub photosynthetic light intensities could be used to alter the relative production of lipid classes in a commercially useful manner. Nor had it been proposed that sub photosynthetic light intensities could be utilized to alter the localization of EPA in lipid reservoirs of microalgae in a commercially useful manufacture.

Extraction of Polar Lipids from Microalgae

Several techniques of potential industrial utility have been proposed for extraction and concentration of galactolipids and/or fatty acids from galactolipid fractions of biological material. Winget (U.S. Pat. No. 5,767,095) describes in detail a range of extraction and concentration techniques used to recover particular lipid classes, including relatively pure galactolipids containing EPA, from a number of photosynthetically produced microalga including those of the diatom genus *Chlorella*.

Cohen et al (J. Appl. Phycol. 5: 109., 1993.) disclose the fatty acid DHA may be produced from the phosphatidylethanolamine (PE) lipid fraction of the photosynthetic organism *Isochlysis galbana* by extracting total lipids and subsequently producing DHA rich compositions by employing the well known technique of urea crystallisation. Vali et al U.S. Pat. No. 6,953,849 disclose a process involving dewaxing of rice bran and hexane extraction and includes HPLC with a silicic acid column. Colarow U.S. Pat. No. 5,284,941 discloses a method involving solvent boric acid gel separation. Buchholz et al U.S. Pat. No. 5,440,028 discloses a method isolation through membrane separation, with pH adjustment. Bergqvist et al 1995 report after their work on oat kernels that galactolipids may be commercially extracted from a range of biological materials using a solid phase extraction using the known differences in solubility in acetone between phospholipids and glycolipids. They started with a hot ethanol extraction then used hexane then hexane/acetone then acetone.

No prior art publications are known to teach that it is possible to selectively isolate EPA-rich compositions in a commercial manufacture from the lipids of organisms that have been cultured using largely heterotrophic culture capable of enhancing EPA productivity and simultaneously increasing the concentration of EPA in specific polar lipid fractions.

Enzymatic Purification

A number of prior art publications disclose the use of enzymes to liberate lipids and arrive at concentrated and purified lipid and fatty acid containing compositions from fish oil and other starting materials. The inventors appreciate that various lipases and phospholipases are capable of disassembling lipids. For example a variety of solvent-based extraction systems and crystallisation techniques have been disclosed that favour extraction of lipids of a particular class or fatty acids of a particular chain length or degree of unsaturation. These enzymes which may include lipases and proteases are known to act preferentially on different substrates. In the case of lipases for example, enzymes are expected to some degree to be specific for lipid class, fatty acid, and the position of the fatty acid within the lipid class. The activity and preference of enzymes can be altered by altering environmental conditions such as temperature, and via the addition of cofactors and techniques such as immobilization.

A common analytical technique used to estimate the localisation of fatty acids at different positions in the lipid structure is to expose a fatty acid class to a lipase capable of selectively hydrolysing fatty acids located in a particular position. It follows that the common general knowledge of those skilled in the art includes the recognition that both the proportion of lipids and the localisation of target fatty acids as well as co-localisation or lack thereof of undesired acids within lipid reservoirs of a biological material constitute critical aspects in a purification process at an analytical scale. To our knowledge however no previous authors have disclosed methods of producing therapeutic or prophylactic compositions via the selective enzymatic hydrolysis of algal polar lipids at least not from polar lipids produced in largely heterotrophic cultures.

Applications of Galactolipids

Winget teaches use of topically applied MGDG-EPA compositions in the prevention and treatment of inflammation, but does not disclose application of lipase-type or indeed any enzymes. Later, Bruno et al (Eur J Pharmacol: 524; 159-168 7 Nov. 2005) disclose that the galactolipid classes MGDG, DGDG and SQDG obtained from thermophilic blue-green algae have in-vivo anti-inflammatory activities in a croton-oil induced mouse ear inflammatory response. However there is no indication in the abstract that any of the n-3 HUFAs were present.

OBJECT

The present invention provides novel methods for obtaining EPA-rich compositions that provide the public with a useful choice. In addition, the present invention provides compositions including EPA-rich galactolipids and highly purified EPA-rich fatty acid compositions that provide the public with a useful amount of therapeutic, prophylactic, or dietary EPA, or at least provides the public with a useful choice.

STATEMENT OF INVENTION

In a first broad aspect the invention provides a process for obtaining an eicosapentaenoic acid (EPA)-rich composition for therapeutic or prophylactic use, wherein the process employs a culture of micro-organisms of a type selected for a capability of largely heterotrophic growth, and a capability of production of EPA, and a capability of photosynthetic lipid production; the process including a culture phase in which cells are grown under conditions in which organic carbon is used as an energy source; the conditions including use of controlled illumination at a level corresponding to an average photosynthetically active irradiance inside the culture of less than 40 μmol photons $m^{-2}$ $s^{-1}$ and including imposition of limitation of nutrients selected from a range including phosphorus and silicon; said procedures being undertaken in order to maximise the amount of recoverable polar lipids including at least one EPA side chain, and a harvesting process that creates a composition rich in EPA.

In a related aspect the invention provides a process as previously described in this section wherein the culture of micro-organisms comprises identified microalgae, fungi or bacteria.

Preferably the micro-organisms are comprised of the marine single-celled diatom known as *Nitzschia laevis*, University of Texas microalgal collection UTEX 2047.

In another related aspect, the micro-organisms comprises a strain of micro-organism selected, when under culture conditions, for an improved yield of recoverable polar lipids having molecules which include at least one side chain bearing EPA.

Preferably the micro-organisms accumulate galactolipids rich in EPA concentrated at the Sn1 position within the galactolipid or like classes.

More preferably the micro-organisms are capable of accumulating commercially useful quantities of polar lipids, including galactolipids rich in EPA at the same time as exhibiting high EPA productivity in general, including the EPA found in triglycerides.

In particular, the EPA-rich lipid classes contained in the total lipid fraction include without limitation one or more of the following: MGDG; MGMG; DGDG; DGMG; non-galactosyl polar lipids including PC and PG; neutral lipids including monacylglycerol, diacylglycerol, triacylglycerol.

Preferably the culture is capable under managed conditions of producing a proportion of its total dry weight as fatty acids; the proportion lying in the range of between 5 and 80%. Preferably the culture is capable under managed conditions of producing a proportion of its total fatty acids as EPA; the proportion (by dry weights) lying in the range of between 1 and 80%. Preferably the culture is capable under controlled conditions of producing 25% to 60% of total fatty acids as fatty acids contained in polar lipids; more 380 preferably the proportion is more than 30%, more preferably over 40% and even more preferably over 50%.

Preferably the organic carbon component is fed incrementally over time, according to the future predicted growth of the culture in a period of 4 to 24 hours.

Preferably the culture is capable under controlled conditions of producing 5 to 40% of total fatty acids as fatty acids contained in galactolipids; more preferably the proportion is more than 10%, more preferably over 20% and even more preferably over 30%.

Preferably the culture is capable under controlled conditions of producing 40 to 70% of EPA as EPA contained in polar lipids (as distinct from neutral lipids); more preferably the proportion is more than 50%, more preferably over 60%.

In a second broad aspect the invention provides an EPA-rich composition derived from a culture as previously described in this section, wherein the EPA-rich compositions are obtained by a harvesting process including the steps of:

harvesting cells from the culture medium at a selected time;
heat or otherwise killing the cells to denature endogenous enzymes;
forming the cells into a cake of biomass;
extracting the cake of biomass with a first, non-selective lipid solvent and recovering the extracted material from the solvent as a residue; (use of near critical di-methyl ether is one option)
extracting the residue with a second, selective solvent so that a neutral, EPA-rich lipid composition is separated from the polar, EPA-rich lipid composition and optionally further purifying either or both types of EPA-rich compositions in order to achieve a required standard of purity.

In a related aspect the invention provides an EPA-rich composition derived from a process as previously described in this section, wherein the method includes a procedure in which EPA is hydrolysed from a polar EPA-rich lipid class obtained from the polar EPA-rich lipid fraction using the steps of:

presenting the polar lipid as a substrate to at least one enzyme capable of cleaving EPA from the Sn 1 position and after cleavage separating the EPA as a free or esterified fatty acid or metal-salt, thereby obtaining an EPA composition intended for use as a therapeutic composition or for prophylactic use.

Preferably the enzymic process uses at least one enzyme selected from the range of lipases, phospholipases and galactolipases. Optionally the enzyme is affixed to a surface.

Alternatively the recovery of fractions having a relatively high EPA purity and an increasing yield is accomplished by matching the enzymic release of fatty acids over time with a series of recovery steps in a continuous or multistage batch extraction process.

Alternatively, the addition of materials including (without limitation), an alcohol, hexane or calcium chloride may assist enzymic release by removing products of the enzyme-catalysed reactions from proximity of the enzyme.

Optionally physico-chemical fractionation of the polar lipid fraction, including techniques such as partitioning, chromatographic fractionation and the like, may precede the application of one or more enzymes.

Preferably said galactolipids rich in EPA will be contained in preparations of the biomass of organisms.

More preferably said galactolipids rich in EPA will be contained in the total lipid fraction extracted from the biomass of organisms from which fraction they may be subsequently separated from the total lipid fraction.

In a first related aspect the invention provides a first method for isolating useful products comprising the steps of: (a) taking a preparation of the biomass of the cultured organisms, (b) extracting the total lipid fraction from the biomass, and (c) isolating one or more lipid classes contained in the total lipid fraction including but not limited to one or more of the following classes: MGDG; MGMG; DGDG; DGMG; SQDG; non-galactosyl polar lipids including PI, PE, LPC, PC and PG; neutral lipids including monoacylglycerol, diacylglycerol, triacylglycerol.

Alternatively, the EPA is concentrated in galactolipid classes which are the preferred substrate of and/or able to be made accessible to an enzyme capable of hydrolyzing one or more acyl bonds and thereby liberating the EPA contained within the galactolipid classes.

In another alternative, EPA is concentrated within the diacyl galactolipid classes.

More preferably EPA is concentrated within the monogalactosyldiacylgalactolipid (MGDG) class.

Preferably the EPA-rich composition is processed after separation in order to further purify the composition, using known techniques though usefully not having to contend with DHA.

Preferably the undesired molecules (even if present) are not cleaved from the polar lipid, so that (for example) the EPA composition is substantially free of DHA which remains acylated to the glycerol backbone.

Preferred known techniques for separation include low temperature crystallisations, purification processes taking advantage of differential solubility of fatty acid esters or salts in various solvents including ionic solvents, precipitation using metal salts, the use of selectively permeable membranes, column chromatography of fatty acids or their esters, supercritical fluid chromatography, urea addition crystallisation, fractional distillation, preparative HPLC, iodolactonization, and selective re-esterification by enzymes.

In a first alternative aspect, the invention provides a composition derived from a process as previously described in this section, wherein the composition comprises 50-60% EPA, less than 5.5% arachidonic acid and substantially no DHA. Preferably the composition comprises 50-60% EPA, less than 4.5% arachidonic acid and substantially no DHA. More preferably the composition comprises 50-60% EPA, less than 3.5% arachidonic acid and substantially no DHA. Even more preferably the composition comprises 50-60% EPA, less than 2.5% arachidonic acid and substantially no DHA.

In a second alternative aspect, the invention provides a composition derived from a process as previously described in this section, wherein the composition comprises 50-60% EPA, less than 5.5% arachidonic acid and less than about 2% DHA. Preferably the composition comprises 50-60% EPA, less than 4.5% arachidonic acid and less than about 2% DHA. More preferably the composition comprises 50-60% EPA, less than 3.5% arachidonic acid and less than about 2% DHA. Even more preferably the composition comprises 50-60% EPA, less than 2.5% arachidonic acid and less than about 2% DHA.

In a third alternative aspect, the invention provides a composition derived from a process as previously described in this section, wherein the composition comprises 60-70% EPA, less than 4.5% arachidonic acid and substantially no DHA. Preferably the composition comprises 60-70% EPA, less than 3.5% arachidonic acid and substantially no DHA. More preferably the composition comprises 60-70% EPA, less than 2.5% arachidonic acid and substantially no DHA. Even more preferably the composition comprises 50-60% EPA, less than 1.5% arachidonic acid and substantially no DHA.

In a fourth alternative aspect, the invention provides a composition derived from a process as previously described in this section, wherein the composition comprises 60-70% EPA, less than 4.5% arachidonic acid and less than about 1.5% DHA. Preferably the composition comprises 60-70% EPA, less than 3.5% arachidonic acid and less than about 1.5% DHA. More preferably the composition comprises 60-70% EPA, less than 2.5% arachidonic acid and less than about 1.5% DHA. Even more preferably the composition comprises 50-60% EPA, less than 1.5% arachidonic acid and less than about 1.5% DHA.

In a fifth alternative aspect, the invention provides a composition derived from a process as previously described in this section, wherein the composition comprises between 95 and 99% EPA, less than 1% of arachidonic acid and less than about 0.5% of DHA.

In a sixth alternative aspect, the invention provides a composition derived from a process as previously described in this section, wherein the composition comprises between 95 and 99% EPA, less than 0.5% of arachidonic acid and less than about 0.5% of DHA.

In a seventh alternative aspect, the invention provides a composition derived from a process as previously described in this section, wherein the composition comprises between 95 and 99% EPA, less than 1% of arachidonic acid and less than about 0.1% of DHA.

In an eighth alternative aspect, the invention provides a composition derived from a process as previously described in this section, wherein the composition comprises between 95 and 99% EPA, less than 0.5% of arachidonic acid and less than about 0.1% of DHA.

In a ninth alternative aspect, the invention provides a composition derived from a process as previously described in this section, wherein the composition comprises between 99.6 and 99.9% EPA, less than 0.1% of arachidonic acid and less than 0.1% of DHA.

In a further alternative aspect the invention provides for use of a composition, as previously described in this section, in the manufacture of a medicament for treatment of a person affected by certain medical conditions or disorders including but not limited to those selected from diabetes (type I, and type II), glycaemic disorders diabetes-associated hypertension, cancer, osteoarthritis, autoimmune diseases, rheumatoid arthritis, inflammatory and auto-immune diseases other than arthritis, respiratory diseases, neurological disorders, neurodegenerative disorders (including Huntington's disease, Parkinson's disease, Alzheimer's disease, schizophrenia, major depression, unipolar depression, bipolar depression, obsessive compulsive disorder, borderline personality disorder, post natal depression, organic brain damage, and traumatic brain injury), renal and urinary tract disorders, cardiovascular disorders, cerebrovascular disorders, degenerative diseases of the eye, psychiatric disorders, reproductive disorders, visceral disorders, muscular disorders, metabolic disorders, prostatic hypertrophy and prostatitis, impotence and male infertility, mastalgia, male pattern baldness, osteoporosis, dermatological disorders, dyslexia and other learning disabilities, cancer cachexia, obesity, ulcerative colitis, Crohn's disease, anorexia nervosa, burns, osteoarthritis, osteoporosis, attention deficit/hyperactivity disorder, and early stages of colorectal cancer, lung and kidney diseases, and disorders associated with abnormal growth and development.

In a third broad aspect the invention provides a composition prepared as previously described in this section, wherein the composition is prepared in the form of a human dietary supplement for therapeutic or prophylactic use.

In a first (therapeutic) alternative, the invention provides for use of a polar lipid, prepared as previously described in this section and including an effective amount of EPA in the manufacture of a medicament for use in treating the medical conditions or disorders as previously listed in this section.

Preferably the polar lipid is formulated in order to provide a prophylactic, health or dietary daily health supplement including an amount in the range of from 0.1 to 50 grams of EPA.

Alternatively the amount is in the range of from 0.5 to 5 grams of EPA.

(Note that even if an EPA-rich polar lipid composition suitable for food and dietary supplement use has a relatively low content of EPA; it is a relatively high ratio of EPA to undesirable molecules that renders the composition fit for purpose, since the undesired molecules exist at a substantially low level in the composition).

Preferably the content of EPA in the relatively low purity composition is less than about 20% and the content of undesired molecules remains low even if the purity of the EPA is below 20%.

In a yet further preferred aspect, the invention provides one or more relatively low purity EPA compositions which are nevertheless pharmaceutically effective owing to a substantially low level of undesired molecules in one or more lipid fractions.

More preferably the content of EPA between about 10% and about 80%.

Preferably the availability of such polar lipid compositions broadens the choice of compositions having a high ratio of EPA to undesirable molecules which is currently restricted to highly purified EPA from fish oil, which is less accessible to the general population.

More preferably the amount is formulated so as to be suitable for repeated ingestion as a prophylactic, health or dietary daily health supplement.

Preferably the products when consumed are capable of promoting brain and mental health, cognition and behaviour.

Preferably the products when consumed are capable of eliciting health promoting effects on any of the following non limiting list of body systems and tissues; auditory, appetite, arousal, balance, blood, bone, bowel, cardiovascular, digestive, endocrine, enteric, emotional, gastric, hair, hepatic, immune, lymphatic, kineaesthetic, marrow, memory, metabolic, musculoskeletal, neurotransmitter, nasopharyngeal, pancreatic, musculoskeletal, reproductive, respiratory, ocular, oesophagal, olfactory, palate, pulmonary, proprioceptive, renal, skin, sleep, stomach, sensorimotor, skin, urinogenital, wound healing.

In a further alternative, the prophylactic, health or dietary supplement is formulated as a solid substance compatible with direct ingestion by humans; the range of formulations including: a cake, a powder, granules, tablets, boluses, pills, capsules, lozenges or beads.

In one option, the EPA is re-esterified or combined with polar lipids, or alternatively the EPA moiety is cleaved from the galactolipids and re-esterified into phospholipid fractions.

More preferably intact or semi-intact polar lipids rich in EPA are capable of efficiently passing through endothelial and other peripheral cell membranes in mammals.

Preferably said polar lipid fatty acids are incorporated into cell membranes within the mammal.

A prophylactic, health or dietary supplement as previously described in this section, wherein the health supplement is provided as a liquid substance carrying finely dispersed EPA-rich extracted polar lipids suitable for consumption as a beverage; the range of beverages including, (without limitation) water, beer, wine, milk, spirits, sports drinks, juices and carbonated drinks, and optionally includes at least one stabilizing substance.

Preferably the EPA-rich extracted polar lipids are encapsulated such that n-3 HUFAs and other PUFAs are protected from light including ultraviolet light in order to assist long-term stability.

Preferably the EPA-rich extracted polar lipids are encapsulated such that n-3 HUFAs and other PUFAs are protected from oxidative degradation.

Optionally, in the case of beverage preparations, the EPA-rich extracted polar lipids (including galactolipids) will be released into the beverage from a temporary encapsulation shortly prior to consumption.

A prophylactic, health or dietary supplement as previously described in this section, wherein the health supplement is formulated as a substance selected from the range including: a solution, a suspension, a solid mass, a powder, granules, or the like; the substance including an effective amount of an extracted galactolipid class rich in EPA and, when in use, is compatible with incorporation into a manufactured foodstuff.

An EPA-rich composition suitable for use as an EPA-rich human or animal dietary supplement derived as previously described in this section, wherein the process includes the steps of obtaining the cake of biomass as harvested from the culture, and of preparing substantially the entire biomass for consumption.

In a yet further alternative, the residual whole cell content is utilized as a product in particular suitable for use as a food for mammals including monogastric and ruminant animals and/or aquaculture species including fin fish and crustaceans; there being valuable residual compounds e.g.—sulpho galactolipids, carotenoids, other pigments, amino acids, and other fatty acids capable of serving as foods.

Optionally a method for extracting EPA from a biomass derived from procedures whereby certain biomasses produced via the use of in vitro techniques accumulate commercially useful quantities of galactolipids rich in EPA at the same time as exhibiting high EPA productivity when grown under conditions according to those previously described in this section, in relation to the first broad aspect, may commence by first removing undesired fatty acids or lipids with a relatively low EPA content, and later extracting the EPA.

In a fourth broad aspect the present invention discloses a pharmaceutically pure composition of EPA, wherein the fatty acid composition of the composition preferably contains (a) about 80 to 100% EPA and (b) little or no other omega 3 or omega-6 fatty acids; such compounds being useful in the treatment of those medical conditions that respond to medication with EPA.

Preferably, but not solely, the pharmaceutically pure composition of EPA is derived from galactolipids.

Preferably said pharmaceutical compositions will contain EPA as at least 90% of total fatty acids in the composition and may be substantially pure EPA.

Preferably the content of any one of the fatty acids selected from the non-limiting range of undesirable compounds including: DHA, AA, DPA, 18:4 n-3, 18:3 n-3, 18:2 n-6 is less than 2% of total fatty acids in the composition and more preferably approaches zero.

In a related aspect these EPA compositions will contain very low or undetectable levels of undesirable molecules which are either structurally similar to, or biologically related to, or antagonistic to the desired effects of EPA when administered to a mammal.

PREFERRED EMBODIMENT

The description of the invention to be provided herein is given purely by way of example and is not to be taken in any way as limiting the scope or extent of the invention. Throughout this specification unless the text requires otherwise, the word "comprise" and variations such as "comprising" or "comprises" will be understood to imply the inclusion of a stated integer or step or group of integers or steps but not the exclusion of any other integer or step or group of integers or steps.

Most approaches to culturing single-celled organisms for EPA production have been based on solely heterotrophic culture, or else cultures grown under conditions providing substantial levels of light; substantially daylight or artificial equivalents. The present invention includes a novel culture-related aspect, wherein polar lipids rich in EPA are co-produced together with neutral lipids in cultures that are largely heterotrophic in that they are mixotrophic cultures producing using significantly lower photosynthetically active average irradiances inside the culture. These will optimally be sub-photosynthetic (i.e., less than 10 µmol photons $m^{-2}$ $s^{-1}$) but may be as high as 40 µmol photons $m^{-2}$ $s^{-1}$.

The invention exploits the tendency for EPA productivity in polar lipids to increase and for EPA to become localised within particular polar lipid classes under these conditions. Compositions are provided that facilitate subsequent purification of EPA-rich lipid classes, or may be directly incorporated into novel supplements rich in EPA.

Galactolipids are incorporated as a major structural component of the membranes of chloroplasts. Other polar lipids including phosphatidyl choline (PC) are also involved in transfer of EPA to the chloroplasts. Certain types of marine algae, but not all, generate intracellular chloroplasts if illuminated and so would be expected to generate these photosynthetic lipids in response to light. The invention takes advantage of the non-linear relationship between provision of light and subsequent production of photosynthetic lipids.

The inventors are aware that the neutral fraction of lipids will also contain significant amounts of EPA. This material is likely to be of commercial value in itself and fatty acid derivatives thereof could be purified by traditional or emerging methods mentioned below to give an EPA product. Thus the present invention should be seen as an adjunct to neutral lipid production rather than a replacement.

Low light levels lie in a range wherein organic carbon consumption is reduced or the efficiency of its use is improved, yet without the technical complications of providing high levels of light either by use of outdoors culture with technical and environment-related complications or by the use of large amounts of artificial light with associated energy costs to be met.

As well as largely heterotrophic cultures grown under conditions of low light a further option is the induction of nutrient depletion in cultures in order to encourage particular types of polar lipid production. Such induced deficiencies include phosphate deficiency which are expected to shift lipid production from phospho- to galacto-lipids. Silicate depletion in diatoms is also contemplated by the invention as a means of causing photosynthetic lipids to accumulate.

The invention makes use of the specific molecular structures of certain polar lipids in certain organisms under certain conditions in order to facilitate purification of EPA. In association with the above structural specificity, the invention contemplates the use of particular enzymes having specific appetites such as stereospecificity in order to facilitate purification. In addition, the unique physiochemical properties of photosynthetic polar lipid classes produced, including the polar nature of the galactolipid molecules, provides useful methods of administering EPA.

Finally the invention discloses formulations including the EPA and galactolipid-rich compositions and applications for the formulations.

Sources of the Cultured Cells

The particular micro-organism that has been used in the procedures described at the time of filing this specification is *Nitzschia laevis*. Cells were obtained from the University of Texas Microalgal Collection where they are deposited with the call reference UTEX 2047. We expect there to be other micro-algae capable of largely heterotrophic growth of the "coloured" set (those having photosynthetic machinery) to exhibit comparable or improved rates of production. At this time, we have not carried out any strain selection experiments designed to encourage expression of superior metabolic profiles under an imposed set of artificial culture conditions, and which allow cells having those profiles to be isolated. We would, however, expect a measurable gain in process efficiency (with regard to EPA production) to result.

At this point, trials with (a) other micro-algae, (b) selected micro-algae, (see above) or (c) genetically modified micro-algae (see "variations") have not been done although all such trials are included in the scope of the invention.

Scaling of Production

Large scale commercial cultures of microalgae can be produced according to the methods of this invention under closely monitored and controlled conditions in a vessels with capacities measured in tens or hundreds of thousands of liters. Changes in conditions and requirements associated with the scale of the culture vessel (e.g. cooling/heating, mixing, gas mass transfer) would be anticipated by those skilled in the art.

Further Purification of EPA

Once material with a relatively high level of EPA has been obtained it may be purified further by a number of means. These include low temperature crystallisations, purification processes taking advantage of differential solubility of fatty acid esters or salts in various solvents including ionic solvents, precipitation using metal salts, the use of selectively permeable membranes, column chromatography of fatty acids or their esters, supercritical fluid chromatography, urea addition crystallisation, fractional distillation, preparative HPLC, iodolactonization, and selective re-esterification by enzymes.

Enzymes and their Provenance.

An "ideal enzyme" for use in the invention would be able to excise side chains from the glycerol backbone of any polar lipid class if the side chain comprises a EPA. Whilst several lipases have been isolated that show selectivity for chain length we know of no cases where absolute specificity based on chain length has been demonstrated. None of these enzymes is currently available for industrial processes.

Many known lipases have the restricted ability of being able to act at the Sn1 position only, which suggests the production and isolation of polar lipids having a desired n-3 HUFA predominantly at the Sn1 position would be a route to enrichment. Selection of a particular enzyme for use in a commercial process is also cost-dependent and it may be necessary to rely on those lipase-type enzymes already produced in bulk for use in the dairy industry or the baking industry, which includes 1,3 specific lipase-type enzymes made from fungi—for instance the lipase/phospholipase derived from *Aspergillus* spp, "Bakezyme PH 800 BG" (DSM Food Specialities), or the lipase derived from *Rhizopus oryzae*, "Piccantase® R8000". The engineered enzyme "Lecitase Ultra" (Novozymes) has 1,3 specific lipase activity but at elevated temperatures demonstrates phospholipase A1 activity. Both activities are likely to be of use in the isolation of fatty acids from the Sn1 position of polar lipids.

At this time, attention has been applied in particular to phospholipases. However it will be appreciated that other lipases and galactolipases are also of relevance in the extraction of EPA and of EPA-containing materials from biomass. Clearly there is an opportunity for further exploitation and optimisation of enzyme specificity within the invention, for it is likely that enzyme-based purification will have a number of advantages over physico-chemical separation of fatty acids. Tasks such as separation of DHA from DPA or 18:2 from 18:4 fatty acids are relatively difficult under existing methods many of which are hampered by reliance on physico-chemical factors such as melting points or molecular sizes.

The current specification discloses a method to produce a relatively pure EPA composition by exposing a microalgal biomass rich in galactolipid EPA to an enzyme.

In some versions of the commercial process disclosed herein it is likely that any enzymes used will be adsorbed on to a surface or otherwise retained within the process, in order to conserve supplies, by the use of techniques for handling enzymes that are well known in the art. It is also likely that optimisation of working conditions for a selected enzyme will provide a significantly improved rate of attack and a more specific type of attack, as a result of exploitation of working conditions well known to those skilled in the art, such as concentration, pH, temperature, presence of salts, or the presence of competing compounds that inhibit undesired modes of action.

In general terms the polar lipids can be either (A) isolated as particular types, or (B) used as one, collective group. For either A or B, they may then be (i) used directly, (ii) further processed into EPA-rich fatty acid compositions by cleaving the fatty acids from the lipid species. In the case of further processing, a polar lipid fraction or fractions may be hydrolysed with a specific phospholipase (or other lipase), the released EPA captured by a suitable acceptor molecule. Examples of acceptors include: glycerol and alcohols including ethanol, propanol, iso-propanol, or long-chain alcohols (which will yield waxes). Alternatively, the EPA may be transferred by a phospholipase, galactolipases, or other lipase on to a suitable carrier type molecule (such as phosphatidylcholine (PC)). Metal salts membrane separation.

Typical Applications

Typical applications include, for (i): production and use of ultra pure EPA and an active pharmaceutical ingredient (ii) production and use of non-pharmaceutical EPA-only therapeutic compositions (iii) production and use of EPA-rich polar lipid containing foods, functional foods and food supplements, and (iv) production and use of whole-cell products for foods or food supplements.

Example 1

Mixotrophic Batch Cultures of *N. laevis*

Actively growing cells of the species *N. laevis* obtained as above are produced in 200 mL of media in stoppered 500 mL Erlenmeyer flasks. Multiple flasks are used to produce large volumes of material. An inoculum of 0.2 g $L^{-1}$ of exponential or early stationary phase cells is used. Flasks are incubated in temperature- and light-controlled growth chambers by placing them on orbital shakers at around 200 rpm to maintain the cells in suspension and aid in gas transfer between atmosphere and media. Temperature is maintained at 20° C. Light is provided at an average irradiance of photosynthetically active light in the culture of 40 μmol photons $m^{-2}$ $s^{-1}$ as measured by an Apogee quantum sensor digital pyranometer and calculated from conditions such as culture depth and cell density. Aliquots of culture are taken during growth to determine the dry weight of the culture at that time point. Cultures are fed a heat sterilised glucose stock solution (400 g $L^-$) daily at a level that is projected to provide organic carbon requirements for the predicted biomass production over the subsequent 24 hours. Total glucose added to culture over the entire culture period amounted to 3 grams per liter.

Culture Medium

Initial concentrations of nutrients in standard media are typically, per liter:

(a) 50 ml Salt stock solution which comprises NaCl; 160.0 g, $MgSO_4$ $7H_2O$; 44.0 g, KCl; 10.8 g, $CaCl_2$; 2.04 g, $KH_2PO_4$; 0.8 g per 1 L of distilled water.

(b) 50 ml Nitrogen stock solution, which comprises the following: NaNO3; 17 g, and yeast extract; 16 g per liter of distilled water.

(c) 10 ml Tris buffer stock solution. This stock is made by dissolving 89.2 g Tris buffer in 1 L distilled water.

(d) 5 ml Trace Metal stock solution, which contains the following, per 100 ml; (NH4)6Mo7O24 $4H_2O$; 0.556 g, CoCl2 $6H_2O$__0.046 g, MnCl2 $4H_2O$__0.500 g, Na2Mo04 $2H_2O$__0.048 g, H3BO3__61.120 g, ZnCl2__0.622 g, H2SO4 (concentrated); 18 ml.

(e) 2 ml of vitamin solution which is made by dissolving 6 g 0.1% vitamin B12, 0.01 g Biotin and 0.01 g Thiamine in 100 ml distilled water.

(f) 5 ml Sodium Metasilicate stock solution which is made by dissolving 24 g Na2SiO3 in 1 L distilled water).
(g) 2.7 ml of Chelated Iron stock which is made by dissolving 0.81 g FeCl3 6H$_2$O in 10 ml of 0.1N HCl and dissolving 10 g NaEDTA in 100 ml 0.1N NaOH.
(h) 1 mL Copper sulphate stock which is made by dissolving 9.8 mg CuSO$_4$ 5H$_2$O in 1 L distilled water.

Biomass Dry Weight Determination

Biomass dry weight is measured, using the pre-weighed glass fibre filter method as follows. A 10 ml sample is removed from a larger representative sample taken whilst stirring to achieve a broadly homogenous dispersion of cells and cell aggregates; culture flasks are generally sterilised with a Teflon-coated magnetic stir bar in place to aid with this. The 10 ml sample is placed in a centrifuge tube and spun at 3000 rpm in a Heraeus Sepatech Megafuge 1.0 with swing-out rotor for 4 min and the liquid decanted leaving a cell pellet. The cell pellet is washed with phosphate-buffered saline and re-centrifuged. A Sartorius glass fibre filter is washed by passing 1 liter of deionised water through the filter then dried overnight in a vacuum oven at 30° C. prior to being weighed. The 10 ml sample is passed through the preweighed filter in a vacuum filter apparatus and is then placed in an oven at 60 deg C. for two hours prior to being reweighed. The difference in grams between the pre and post weights times 100 is taken as a measure of the dry weight per liter.

Harvesting and Extraction of Lipid-Containing Material.

Cells are harvested after 3 days of growth since at this point the culture(s) are still in exponential phase. Cellular extract containing the lipids can be obtained by Folch extraction following the method of Bligh and Dyer (1959). Cells from several flasks are combined to allow production of sufficient material for further use.

Total Fatty Acid Analysis.

Total fatty acid analyses of samples of cellular extract are obtained to identify the composition of the cultured material. Addition of an internal standard such as C23:0 to the reaction allows measurement of the total fatty acid content of the cells. The method of fatty acid production entails a basic transesterification with 0.5M methoxide in methanol followed by an acidic transesterification using dry HCl in methanol. Fatty acid methyl esters are recovered by extracting with hexane and drying with sodium sulphate before analysis using gas chromatography. The sample is run on a 30 m×0.25 mm ID Framewax (crossbond polyethylene glycol) glass capillary column contained within a Shimadzu 2010 GC by autoinjection. By ramping the column temperature from 145 to 240° C. over the course of 50 minutes and then leaving the column at 240° C. for a further 10 minutes fatty acids is identified by co-chromatography with known standards supplied by Restek.

Lipid Separation.

Cellular extract is separated into polar and non-polar fractions using column chromatography. 0.5-2 g of the cellular extract is dissolved in a small volume of diethyl ether and loaded onto a column containing 40 g silica gel (with a mesh size of 230-350) in diethyl ether. 10 mL of diethyl ether and 80 mL of chloroform is used to elute non-polar material including the triglycerides. Further addition of 10 mL chloroform:methanol (1:1 v/v) and 80 mL methanol to the column elutes the polar material including galactolipids and phospholipids. These two classes of material are collected separately and dried down before samples are subjected to fatty acid analysis similar to that described above. The polar fraction is then further separated by placing it on a second chromatographic column. A column is constructed of silica gel in chloroform and is washed with successive washes of 2 column volumes each of 99:1 (v/v), 49:1 (v/v), 29:1 (v/v), 19:1 (v/v), and 9:1 (v/v) chloroform:methanol and 2 column volumes of methanol. Further steps are added as required to separate other galactolipids and phospholipids from one another if so desired.

Lipase Based Separation of Fatty Acids from Specific Positions within Lipid Molecules.

The 1,3 specific lipase and phospholipase A1 "Lecitase Ultra®" from Novozymes is used to cleave the fatty acids from the Sn-1 position of MGDG isolated in the manner described above. 5 mg of MGDG is dissolved in 3 mL of methanol whilst 12 u of enzyme is dissolved in 3 mL 10 mM citric acid buffer at pH6.0. These are incubated together at 60° C. for 5-15 minutes and after incubation the reaction could is washed 3 times with 2 mL hexane to collect the free fatty acids produced. The hexane washes are collected in a fresh tube with 3 mL methanol and the mixture incubated at 50° C. for 2 hours to produce Fatty acid methyl esters. At the end of this period the hexane layer is removed and concentrated before being analysed on a GC.

Results.

After 72 hours a biomass dry weight reaches 3 grams per liter in flask culture. Fatty acids form at least 8% of the dry material grown in the culture. EPA reaches 24% of total fatty acids. Cultures of *Nitzschia laevis* grown in this manner demonstrate doubling times as low as 12 hours. The analysis of the fractions recovered from the first chromatographic column shows that roughly equal amounts of fatty acids are recovered in polar and non-polar lipid fractions. 67% of the EPA is located in the polar fraction.

Analysis of the fractions by GC shows that around one third of the polar fatty acids elute in the 9:1 (v/v) fraction, Thin Layer Chromatography of the fractions indicates that the 9:1 (v/v) fraction contains the bulk of the galactolipid MGDG with the remainder of the MGDG and all other lipid classes eluting with methanol.

Table 1 (below) shows in the left hand column the total fatty acid profile of MGDG isolated using the method described in the present example and in the right hand column the total fatty acid profile of fatty acids recovered from the hydrosylate.

TABLE 1

Total and enzyme-hydrolysed fatty acids from MGDG.
Figures are percentage of total fatty acids loaded on the GC. Please note that where results are expressed as "ND" ("not detected") the amount present was beyond the limits of detection of our instrument.

| Fatty acid Name | Total Fatty acid production from MGDG | Enzyme-liberated Fatty acids from MGDG |
|---|---|---|
| C14:0 | 2.44 | 3.81 |
| C16:0 | 3.94 | 2.17 |
| C16:1 c9 | 35.79 | 27.06 |
| C16:2 | 4.07 | 1.62 |
| C16:3 | 14.15 | 0.49 |
| C16:4 | 0.47 | ND |
| C18:2 c9,12 | 0.26 | 0.14 |
| C18:2 t9,12 | 0.04 | ND |
| C18:3 c9,12,15 | 0.48 | 0.89 |
| C18:3 c6,9,12 | 0.22 | ND |
| C18:4 n3 | 0.88 | 0.43 |
| C20:2 c11,14 | 0.09 | 0.76 |
| C20:4 c5,8,11,14 – AA | 2.99 | 5.32 |
| C20:4 c8,11,14,17 | 0.19 | 0.23 |
| C20:3 c8,11,14 | 0.05 | ND |
| C20:5 c5,8,11,14,17 – EPA | 30.11 | 54.93 |
| C22:2 c13,16 | 0.07 | 0.64 |
| C22:5 – DPA | 0.2 | 0.21 |

TABLE 1-continued

Total and enzyme-hydrolysed fatty acids from MGDG.
Figures are percentage of total fatty acids loaded on the GC. Please note
that where results are expressed as "ND" ("not detected") the amount
present was beyond the limits of detection of our instrument.

| Fatty acid Name | Total Fatty acid production from MGDG | Enzyme-liberated Fatty acids from MGDG |
|---|---|---|
| C22:6 – DHA | 0.68 | ND |
| Unknown molecules | 1.75 | 0.21 |
| Other saturates | 0.47 | 0.48 |
| Other monounsaturates | 0.68 | 0.61 |

Discussion

The method allows significant increases in the polar lipid production of the organism to take place over that which is measured in a purely heterotrophic culture (where 75% or more of the fatty acids are seen in the non-polar fraction).

Roughly one third of the polar fatty acid in the example is contained in the MGDG fraction as compared with only around 15% in purely heterotrophic cultures.

Application of the enzyme in the present example provides for enrichment of EPA and the exclusion of DHA from the fatty acids recovered from the hydrosylate as compared to the total fatty acids of the MGDG fraction.

Whilst only 30-35% of the total MGDG fatty acids are recovered in the hydrosylate in the present example 57.0% of the EPA in the sample is recovered by the enzymatic process confirming predominance in the Sn1 position of MGDG.

Example 2

Largely Heterotrophic Batch Cultures of *N. laevis*

Flask cultures of *N. laevis* is produced according to the method of example one except that: 5-10 grams of glucose is added over the course of the culture run. Light is provided at an average irradiance of photosynthetically active light in the culture of 10 µmol photons $m^{-2}$ $s^{-1}$. Harvesting, separation and analysis techniques are all according to the method of example one.

Results

After 72 hours a biomass dry weight reaches between 3 and 5 grams per liter in flask culture. Fatty acids form at least 10% of the dry material grown in the culture. EPA reaches at least 20% of total fatty acids.

Analysis of the fractions obtained from the first chromatographic column shows that 35 to 40% of fatty acids are recovered in the polar fraction and 60-65% in the non-polar lipid fraction. EPA is preferentially located in the polar fraction.

Analysis of the fractions by GC shows that between 30 and 40% of the polar fatty acids elute in the 9:1 (v/v) fraction. Thin Layer Chromatography of the fractions indicates that the 9:1 (v/v) fraction contains the bulk of the galactolipid MGDG with the remainder of the MGDG and all other lipid classes eluting with methanol.

Analysis of the MGDG fraction shows that over 30% of the fatty acids are EPA. Of the material recovered from enzymatic hydrolysis, between 50 and 60% is EPA.

Discussion

More fatty acids were recovered in the non-polar fraction than the polar fraction but the amounts of fatty acids in the polar fraction are still substantially higher (50-200% greater) than those from a similar heterotrophic culture grown in the absence of light. EPA is found as a higher proportion of fatty acids in the polar fraction both in comparison to the non-polar fraction and in comparison to a polar fraction from a totally heterotrophic culture.

Significantly, although the amount of lipids recovered in the polar class is lower as a proportion of the whole when compared to mixotrophic or phototrophic growth, the improved growth rates under largely heterotrophic conditions means that polar and galactolipid yields are equivalent to or better than those of example 1.

Example 3

"Perfusion Culture" Mode of Culturing *N. laevis* Including Variation of Nutrient(s) and/or Exposure to Sub-Photosynthetic Light Intensities Larger volumes of actively growing cells of the species *N. laevis* are grown under closely monitored and controlled conditions in a 20 liter vessel, having an effective working capacity of 18.5 liters. The vessel is internally lined with "Teflon®" and comprise a stirred, jacketed tank. The jacket is provided with hot or cold water as required in order to maintain an internal temperature of 20° C., as sensed by internal probes and 830 controlled with a SCADA device controlling water valves. A mechanical seal admits an impeller shaft of 19 mm diameter, having a 6-blade Rushton impeller at one end, placed near an air sparger, and a marine impellor 250 mm from the end. A 0.25 kW 3-phase 6-pole motor drives the shaft at between 100 and 900 revolutions per minute. Motor speed is controlled with a variable speed drive capable of receiving an analogue signal from the supervisory control device. Pressurised air (1.5 bar) is injected through a sterilizing filter at a rate of between 2 to 10 liters per minute to the air sparger. The air flow is measured with a Dwyer flow meter model TF 2110 and the flow rate is controlled either manually through the use of a regulator or by a "Festo" proportional solenoid controller. Similarly gas outflow from the vessel is measured and regulated. Dissolved oxygen is measured by an oxygen sensor (Broadley-James Corporation, Irvine, Calif.) and the dissolved oxygen maintained at around 50% of saturation via supervisory control feedback loops controlling motor speed and, to a lesser degree, air flow.

The pH of the culture is maintained at pH=8.5 (or at another pH if desired) by using an immersed pH sensor (Broadley-James Corporation, Irvine, Calif.) in a closed control loop, driving a peristaltic pump for the addition of either alkali (as NaOH or KOH) or for the addition of acid (as HCl or Acetic acid) as required.

Concentrations of nutrients, including feed stocks that are sources of nitrogen, silicate, phosphorus, glucose, and organic carbon (e.g. glucose) are separately controlled by feeding sterile stock solutions of desired concentrations aseptically through corresponding peristaltic pumps. Sterile basal media is also supplied to the vessel through an aseptic pump. Culture volume is monitored using a Kubler level sensor and input of basal media or nutrient controlled by the SCADA device.

Precautions related to sterility include operations being conducted in a production environment equipped with an air lock and supplied with filtered sterile air to create a positive pressure directing air away from culture vessels. Staff follow protocols well known to those skilled in the art designed to minimize any accidental introduction of contaminants into the production environment. All stocks that can withstand heating are autoclaved at 121° C. for 15 minutes or 132° C. for 4 minutes. Remaining media is filtered through 0.2 micron filters. All pumps, lines and vessels are steam sterilized prior to use of the apparatus and all exposure of culture or cells to the external production environment is undertaken in a laminar flow cabinet in accordance with sterile technique.

The vessel is inoculated by introducing a freshly growing culture through a previously steam-sterilised manifold in order to achieve an initial concentration of from 0.1 to 1 g per liter of cells in the vessel. Motive pressure for the transfer is provided through displacement of the inoculating culture with sterile air.

An optical density probe is also be immersed in the tank in order to indicate the amount of biomass present in a culture. The culture vessel is also be provided with one or more settling devices, which are external separating funnels into which cells within their medium may be pumped from time to time aseptically via the operation of a peristaltic pump. These devices function by allowing cell-containing media to be pumped into them to settle whilst at the same time permitting spent media, substantially free of cells to be removed in a sterile manner. The suspension rich in settled cells located at the bottom of the settling device is then pumped back into the culture vessel via the alternate operation of a second peristaltic pump. The reduction in total medium volume in the main culture vessel is made up with fresh media, so that excretory products can be taken out of the vessel and fresh nutrients added. The dimensions and volume of the settlers is optimised via deign methodologies well know to those skilled in the art to allow the total volume of the tank to be changed over a 24 hour period via the operation of one or more settlers whilst minimizing the residence time of cells in the settlers.

Means for providing light to the micro-algal cells during culture include one or more of: use of an optically translucent or transparent section of the vessel with a surface illuminated externally, insertion of light guides through ports from the exterior into the culture, insertion of a sterilisable light emitting device (e.g. fibre optics, conventional bulbs or LEDs). Cells can be pumped of cells, using a peristaltic pump or the like, from within the culture medium outside and along tubes that are exposed to a light source. For instance a transparent flat panel vessel illuminated using artificial light is used. Relative amounts of time spent in the main vessel and the flat panel system determine the amount of light that the cells are exposed to.

A low continuous level of exposure using, for example, light guides may be preferable to a high intermittent exposure in an external system. Alternatively cells may be pulsed intermittently with high intensity light so as to achieve an average low intensity over the period of the culture.

A preferred method for the production of *Nitzschia laevis* is the use of low intensity light providing a photosynthetically active average irradiance in the culture of less than 40 micromol photons per square meter per second, An even more preferred method for the production of *Nitzschia laevis* is the use of low intensity light providing a photosynthetically active average irradiance in the culture of 1-10 micromol photons per square meter per second.

The biomass is harvested as a batch after 5 to 9 days of growth and subjected to extraction with supercritical dimethyl ether (DME). In this process cells are first collected and heat killed at 70° C. for 15 minutes to denature endogenous enzymes. The cells are then spray dried to form a powder with less than 10% water content. Supercritical DME (at 60° C. and 40 bar pressure) is then used to extract material from the powder and recovered. Removal of the DME leaves a tar-like extract which contains the lipids as well as pigments and other cellular material. Around 50% of the dry weight is extracted using this method. Subsequent extraction of the complex lipid mixture with supercritical $CO_2$ may also be performed which has the effect of separating polar material (left as a residue in the $CO_2$ process) from non-polar (dissolved in the supercritical $CO_2$). A variety of other methods of isolating lipids are known to those skilled in the art. The total extract or isolated neutral or polar lipid fraction may be used in its own right or fatty acids recovered by direct saponification via methods well known to those skilled in the art. Further chromatographic processes as described in example one can then be utilised as necessary to further purify lipid classes or fatty acid fractions.

Isolation of fatty acids from the Sn1 position of specific polar lipid classes is carried out by dissolving the lipid material in methanol and passing it through a column of immobilised Lecitase Ultra. Addition of hexane to the material flowing from the column isolates the fatty acids hydrolysed by the enzyme. These are then purified further as desired. Productivity of this system is between 5 and 50 mg EPA per liter per hour.

Variations

Transgenic Organisms

The invention may rely on use of higher plants cells normal or transgenic organisms including but not limited to algae, fungi, and bacteria.

Culture Conditions

A possible improvement option involves growing micro-organisms for a period under conditions in which the media is depleted of either silicate or phosphate or both in order to cause the organisms to produce more polar galactolipids in their lipid membranes, which are subsequently extracted. Preferably the nutrient limitation is imposed on the culture over the last phase of growth prior to harvesting.

Cooling of Cultures

The culture may be maintained under temperatures below the previously stated 20 degrees Celsius, and above the freezing point of the culture medium.

One option based on the postulate (whether it is adequate or not) that EPA serves to render lipid membranes more fluid involves growing the micro-organisms for a period under conditions in which the micro-organisms are cooled; perhaps as far as the freezing point of sea water (−1.8 deg C.) in order to cause the organisms to include more EPA either as lipids or as galactolipids in their lipid membranes, which are subsequently extracted. Preferably the cooling is applied to the culture over the last phase before harvesting.

Uses of Extracted Material

Therapeutic Compositions.

There is no reason why a therapeutic composition containing less than (for example) 20% EPA yet having substantial absence of other potentially antagonistic molecules such as DHA AA etc. should not be just as effective as a 100% pure EPA oil (not counting esters). The drive to get substantially 100% purity could be re-expressed as a desire to have substantially none of the "undesired molecules" such as DHA. Therefore, acceptance of (for example a 10 to 95% pure EPA) becomes a matter of satisfying the relevant regulatory authorities. The role of the inventors becomes a matter of exclusion of certain impurities. Further, a therapeutic composition that delivers EPA in a relatively water-soluble form (or a stable emulsion in water) has substantial formulation advantages.

EPA-Rich Foods Including Galactolipids

A basis for making foods, food supplements, nutraceuticals, or therapeutic preparations that rely on the EPA held in polar lipid molecules is that on oral administration of polar lipids rich in EPA to a mammal leads to a significant proportion of their fatty acids being absorbed into the blood stream via enteric lymph vessels thereby bypassing first-pass liver metabolism and thus providing greater bioavailability of the EPA.

In addition the polar nature of the lipids renders this form of EPA, which does not behave as in the same manner as a fatty acid or ester or as a neutral lipid, easier to formulate and to administer. Polar lipids derived from microorganisms would not carry a fishy flavour of the type usually present in fish oil extracts. Galactolipids and certain phospholipids according to the invention are recognised to be of particular utility due to a combination of their high EPA content, low content of other potentially antagonistic molecules and undesirable fatty acids.

The unique physiochemical properties of galactolipids conferred by the hydrophilicity of the polar carbohydrate head group; rendering them excellent surfactants. This latter property will allow the production of a range of EPA-only food and in particular EPA-only beverages due to the ability of the galactolipids to be dispersed as micelles and remain stable over long periods of time in aqueous oil in water solutions. In vitro techniques can accumulate commercially useful quantities of polar lipids and especially galactolipids rich in EPA at the same time as exhibiting high EPA productivity when grown under conditions according to this invention, An EPA-rich galactolipid that has been manufactured from a culture according to the invention may be prepared for storage, shipping and sale as a substance having one of a variety of physical forms such as a solution a suspension (feasible with water), or in a cake, a powder, granules, tablets, boluses, pills, capsules, or beads. In, for example, a powder, the galactolipid may be bound to inert particles (such as of starch) or encapsulated by means well known to those skilled in the relevant arts.

Means to restrict oxidation of the EPA may be included in packaging such as by sparging with nitrogen. In addition microencapsulation for foods may be assisted with phospholipids (such as crude or purified lecithins) so that the EPA is protected The composition includes an effective amount of an extracted galactolipid rich in EPA and is suitable for oral ingestion either directly or after a technical process of food preparation.

Beverages.

In order to deliver a recommended daily intake to a population, a beverage may be a most preferred route since beverages are consumed by most people. Due to the vulnerability of n-3 HUFA and other PUFAs to oxidative degradation it may be preferable to encapsulate the galactolipid such that it is protected from light especially sunlight, and released into the beverage shortly prior to consumption. Alternatively it may be desirable to sparge the liquid containing the galactolipid with an inert gas to prevent exposure of the EPA to oxygen. Carbon dioxide in carbonated beverages may assist dispersion of the galactolipid. Micelles may also hold dissolved carbon dioxide in the case of carbonated beverages and the composition of the micelle may be altered in order to enhance this property. In certain cases it may be preferable to add glycerol to these beverage preparations to optimise the dispersion of the galactolipids and also to provide a more desirable mouth feel for the beverage. Alternatively a water-free concentrate which would be made up by the user with water at or near the time of consumption may be distributed. Steps to minimise oxidation of the n-3 HUFA within the concentrate would have to be taken including the use of light-tight packaging, and microencapsulation of the galactolipid.

Milk is a fairly universally consumed beverage and there are many processed variants of "plain" milk on sale. EPA-supplemented milk is made by adding an EPA-rich galactolipid during processing. The usual practice is to homogenize and pasteurize milk in a single process. In order to minimise exposure of the EPA to heat, the EPA-rich galactolipid is preferably added during or after cooling of the milk.

Spreads.

Spreads may have EPA-rich materials included. Such spreads include the protein-rich type such as yeast extracts, or fat-based spreads such as aioli, butter and margarine, in which water is the dispersed phase. In manufacture, the galactolipid is added either to the fatty component or to the water component and the polar nature of the molecule assists in solubility. Spreads also include jams and jellies. The EPA-rich galactolipid may be added to a jam in the form of an emulsion. More solid preparations include sweets and chocolates. The EPA-rich galactolipid may be added as a fat-soluble component during manufacture preferably after heating in order that the galactolipid is not exposed to heat.

EPA-Rich Solid Foods.

EPA-rich galactolipids may be added to ice cream, for example, along with selected long-chain fatty acid molecules and optionally a phosphatidyl choline (PC) molecule as a carrier. An alternative is to transfer the EPA on to a selected PC molecule using a selective galactolipase/phospholipase. Long-chain lyso-phosphatidylcholine is a possible suitable receptor having advantages in processing and in products. The product formed may be insoluble within the enzyme system which tends to drive the equation towards its formation. Alternatively EPA-rich phosphatidylcholine isolated from the culture may be used.

Whole-Cell Preparations Including Effective Amounts of EPA.

Whole-cell preparations, which may be intact, partially hydrolysed, or lysed, may be incorporated directly into spread-type foods, baking products, processed meats or other food supplements either (i) as is, or (ii) after homogenisation (by shear or pressure) or (iii) controlled enzymatic or chemical hydrolysis to aid proteolysis. The whole cell will offer useful protein and generally high HUFA levels, even if some stripping of EPA has taken place.

ADVANTAGES AND INDUSTRIAL APPLICABILITY

The invention as described herein offers:
1. An industrially upwardly scalable process capable of creating a compound (such as EPA) that is difficult to synthesise, and so at the present time is obtained mainly from the limited resource, marine fish oil, yet is in increasing demand on account of rising populations and better awareness of the consequences of inadequate intake.
2. The preferred light levels (of up to about 80 μmol photons $m^{-2} s^{-1}$ if at a steady rate, or at a higher yet equivalent rate if intermittently provided) are cheaper to provide by artificial means than the level of full sunlight, or to provide if daylight is used
3. A process as above for providing EPA in a variety of purities (suitable for therapeutic use) and importantly, the product includes only traces of the undesired molecule DHA.
4. A culture process for creating EPA from a largely heterotrophic organism that is relatively economical to manage, nourish and supply with energy in a large-scale manufacturing environment.

5. A process as above for co-producing EPA with triglycerides, and within polar lipid compounds (for example, galactolipids) that open up a number of possibilities for therapeutic and prophylactic administration.

6. Acceptable and readily ingested formulations containing useful amounts of EPA (in terms of nutritional and/or therapeutic requirements) within polar lipids.

Finally, it will be understood that the scope of this invention as described by way of example and/or illustrated herein is not limited to the specified embodiments. Where in the foregoing description, reference has been made to specific components or integers of the invention having known equivalents, then such equivalents are included as if individually set forth. Those of skill will appreciate that various modifications, additions, known equivalents, and substitutions are possible without departing from the scope and spirit of the invention as set forth in the following claims.

We claim:

1. A process for producing an eicosapentaenoic acid (EPA)-rich composition comprising:
   i) culturing a micro-organism in a medium under controlled illumination, thereby producing a biomass,
   ii) harvesting the biomass, and
   iii) selectively recovering polar lipids with at least one EPA side chain within the biomass in preference to neutral lipids with at least one EPA side chain within the biomass to produce an EPA-rich composition,
   wherein said micro-organism is a type selected for a capability of largely heterotrophic growth, a capability of production of EPA, and a capability of photosynthetic lipid production,
   wherein said medium comprises organic carbon, phosphorous, and silicon, and
   wherein said controlled illumination is at a level corresponding to an average photosynthetically active irradiance inside the culture ranging from about 1 µmol photons m$^{-2}$ s$^{-1}$ to about 10 µmol photons m$^{-2}$ s$^{-1}$, and
   wherein step i) maximizes the yield of recoverable polar lipids including at least one EPA side chain.

2. The process as claimed in claim 1, wherein the organic carbon is fed incrementally to the medium over time, according to a predicted growth of the culture in a period from about 4 hours to about 24 hours.

3. The process as claimed in claim 1, wherein said micro-organism is a marine micro-organism.

4. The process as claimed in claim 3, wherein the micro-organism is the marine single-celled diatom known as *Nitzschia laevis*, corresponding to University of Texas microalgal collection UTEX 2047.

5. The process as claimed in claim 3, wherein the micro-organism is a strain selected for an improved yield of recoverable polar lipids having molecules which include at least one side chain bearing EPA.

6. The process as claimed in claim 1, wherein step ii) further comprises the steps of:
   a) harvesting cells from the culture medium at a selected time;
   b) heat killing the cells to denature endogenous enzymes; and
   c) forming the cells into a cake of biomass.

7. The process as claimed in claim 1 further comprising hydrolysing EPA from the polar lipids obtained from the EPA-rich lipid composition using the steps of:
   a) cleaving EPA from the Sn1 position of the EPA-rich lipid using at least one lipase-type or phospholipase-type enzyme; and
   b) after cleavage separating the EPA as a free or esterified fatty acid, thereby obtaining an EPA composition suitable for use as a therapeutic composition or for prophylactic use.

8. The process as claimed in claim 1, wherein step iii) further comprises the steps of:
   a) extracting the total lipid fraction from the biomass; and
   b) isolating one or more lipid compositions contained in the total lipid fraction.

9. A process for producing an eicosapentaenoic acid (EPA)-rich composition comprising:
   i) culturing a micro-organism in a medium under controlled illumination, thereby producing a biomass,
   ii) harvesting the biomass, and
   iii) selectively recovering polar lipids with at least one EPA side chain within the biomass in preference to neutral lipids with at least one EPA side chain within the biomass to produce an (EPA)-rich composition,
   wherein said micro-organism is a type selected for a capability of largely heterotrophic growth, a capability of production of EPA, and a capability of photosynthetic lipid production,
   wherein said medium comprises organic carbon, phosphorous, and silicon, and
   wherein said controlled illumination is at a level corresponding to an average photosynthetically active irradiance inside the culture of less than 40 µmol photons m$^{-2}$ s$^{-1}$;
   wherein step i) maximises the yield of recoverable polar lipids including at least one EPA side chain; and
   wherein the micro-organism is the marine single-celled diatom known as *Nitzschia laevis*, corresponding to University of Texas microalgal collection UTEX 2047.

10. The process as claimed in claim 9, wherein the organic carbon is fed incrementally to the medium over time, according to a predicted growth of the culture in a period from about 4 hours to about 24 hours.

11. The process as claimed in claim 9, wherein step ii) further comprises the steps of:
   a) harvesting cells from the culture medium at a selected time;
   b) heat killing the cells to denature endogenous enzymes; and
   c) forming the cells into a cake of biomass.

12. The process as claimed in claim 9 further comprising hydrolysing EPA from the polar lipids obtained from the EPA-rich lipid composition using the steps of:
   a) cleaving EPA from the Sn1 position of the EPA-rich lipid using at least one lipase-type or phospholipase-type enzyme and
   b) after cleavage separating the EPA as a free or esterified fatty acid, thereby obtaining an EPA composition suitable for use as a therapeutic composition or for prophylactic use.

13. The process as claimed in claim 9, wherein step iii) further comprises the steps of:
   a) extracting the total lipid fraction from the biomass; and
   b) isolating one or more lipids compositions contained in the total lipid fraction.

* * * * *